(12) United States Patent
Kendall

(10) Patent No.: US 6,506,952 B2
(45) Date of Patent: Jan. 14, 2003

(54) PRODUCTION OF HEXABROMOCYCLODODECANE OF ENHANCED GAMMA ISOMER CONTENT

(75) Inventor: John K. Kendall, Cedar Park, TX (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/982,708

(22) Filed: Oct. 18, 2001

(65) Prior Publication Data

US 2002/0045783 A1 Apr. 18, 2002

Related U.S. Application Data

(63) Continuation-in-part of application No. 09/876,902, filed on Jun. 8, 2001, now Pat. No. 6,420,617, which is a continuation of application No. 09/373,639, filed on Aug. 18, 1999, now Pat. No. 6,284,935, which is a continuation-in-part of application No. 09/353,181, filed on Jul. 14, 1999, now abandoned, which is a continuation-in-part of application No. 09/253,874, filed on Feb. 22, 1999, now abandoned.

(51) Int. Cl.$^7$ ................................................. C07C 17/02
(52) U.S. Cl. ...................................................... 570/246
(58) Field of Search ......................................... 570/246

(56) References Cited

U.S. PATENT DOCUMENTS

| | | | |
|---|---|---|---|
| 3,544,641 A | 12/1970 | Versnel | |
| 3,558,727 A | 1/1971 | Jenkner et al. | |
| 3,652,688 A | 3/1972 | Olechowski et al. | |
| 3,833,675 A | 9/1974 | Newcombe et al. | |
| 4,301,058 A | 11/1981 | Neukirchen et al. | |
| 4,530,880 A | 7/1985 | Taniuchi et al. | |
| 4,783,563 A | 11/1988 | Taniuchi et al. | |
| 4,849,134 A | 7/1989 | Georlette et al. | |
| 4,918,253 A | 4/1990 | Hermolin et al. | |
| 5,004,847 A | 4/1991 | Beaver et al. | |
| 5,004,848 A | 4/1991 | Beaver | |
| 5,025,110 A | 6/1991 | Beaver | |
| 5,043,492 A | * 8/1991 | Ransford | |
| 5,077,444 A | 12/1991 | Cook, Jr. et al. | |
| 5,246,601 A | 9/1993 | Jensen | |
| 5,292,450 A | * 3/1994 | Beaver | |
| 5,593,619 A | 1/1997 | Bottelberghe et al. | |
| 5,741,949 A | 4/1998 | Mack | |
| 5,770,780 A | 6/1998 | Metz et al. | |
| 5,831,137 A | 11/1998 | Metz et al. | |
| 5,866,731 A | 2/1999 | Watanabe et al. | |
| 5,866,732 A | 2/1999 | Eiermann et al. | |
| 6,284,935 B1 | 9/2001 | Kendall et al. | |

FOREIGN PATENT DOCUMENTS

| | | |
|---|---|---|
| DE | 1147574 | 4/1963 |
| DE | 1222049 | 8/1966 |
| EP | 181414 | 5/1986 |
| EP | 429059 | 5/1991 |
| FR | 1553410 | 1/1969 |
| JP | 4338343 | 11/1992 |
| JP | 4338344 | 11/1992 |

OTHER PUBLICATIONS

CAPLUS Abstract of Japanese Patent 4338343 published 11/92.
WPIDSAbstract of Japanese Patent 4338343 published 11/92.
CAPLUS Abstract of DE Patent 3 447 631 published 1986.
CAPLUS Abstract of FR Patent 1 553 410 published 1969.

* cited by examiner

*Primary Examiner*—Alan Siegel
(74) *Attorney, Agent, or Firm*—Edgar E. Spielman, Jr.

(57) ABSTRACT

Hexabromocyclododecane with enhanced gamma isomer content is produced by brominating cyclododecatriene in a liquid medium comprised of (1) at least 50 wt % of at least one liquid inert organic solvent other than 1,4-dioxane having a solubility in water of at least 1 wt % at 25° C., and (2) water in an amount of up to about 40 wt %, in the presence of (3) about 0.5 to about 30 wt % of bromide ion (Br$^-$), each wt % being based on the total weight of the liquid portion of the liquid medium.

44 Claims, No Drawings

PRODUCTION OF HEXABROMOCYCLODODECANE OF ENHANCED GAMMA ISOMER CONTENT

REFERENCE TO RELATED APPLICATIONS

This is a continuation-in-part of commonly-owned copending application Ser. No. 09/876,902, filed Jun. 8, 2001, now U.S. Pat No. 6,420,617 which is a continuation of application Ser. No. 09/373,639, filed Aug. 18, 1999, now U.S. Pat. No. 6,284,935 B1 issued Sep. 4, 2001, which in turn is a continuation-in-part of application Ser. No. 09/353,181, filed Jul. 14, 1999, now abandoned, which is a continuation-in-part of application Ser. No. 09/253,874, filed Feb. 22, 1999, now abandoned.

TECHNICAL FIELD

This invention concerns an improved process for the production of hexabromocyclododecane. The process enables production of a hexabromocyclododecane product with increased gamma isomer content.

BACKGROUND

Hexabromocyclododecane (1,2,5,6,9,10-hexabromocyclododecane, HBCD) is a well established flame retardant for use in various thermoplastics. HBCD is composed of three isomers conventionally referred to as alpha, beta, and gamma. Of the three isomers, pure gamma has the highest melting point. Mixtures of the three isomers exhibit extended melt point regime, but generally it may be said that increasing the gamma isomer content of an HBCD product increases that product's initial melt point. HBCD products with higher initial melting points are the most desirable in the industry, and numerous methods have been sought to boost the gamma isomer content of HBCD. One such method involves washing, triturating, or recrystallizing the crude HBCD to not only increase gamma content, but to also increase product purity. For example, the crude process product may be repeatedly washed with solvents, such as toluene or alcohol, which will remove tetrabromocyclododecenes and other impurities. Such washing will also remove significant amounts of the alpha and beta isomers which, undesirably, reduces the total yield of hexabromocyclododecane product. It is preferred that the gamma isomer comprise at least 70 wt % of the mix to obtain an acceptable melting point regime.

A principal impurity of hexabromocyclododecane (HBCD) is the underbrominated species, tetrabromocyclododecene. The tetrabromocyclododecene impurities can comprise up to 10 wt % of the hexabromocyclododecane product. Lesser impurities include the side-reaction products formed by the reaction of the brominating agent with cyclododecatriene, viz., brominated cyclododecane and reactive solvent coproducts, e.g., alcohols.

The prior art lists a variety of solvents for HBCD production with the goal of producing an HBCD product with high purity, acceptable gamma isomer content, and good yields. One method to achieving a higher purity/higher yielding HBCD is to increase the proportion of HBCD that exists as the gamma isomer. The gamma isomer has the lowest solubility and highest melting point of the three HBCD isomers. Therefore, enhancing the production of the gamma isomer, and lessening the production of the alpha and beta isomers, is very desirable.

Heretofore HBCD has been produced by the bromination of cyclododecatriene in the presence of a solvent, generally an alcohol, e.g., isobutyl alcohol. The alcohol can be used alone or in combination with a wide variety of co-solvents, e.g., halogenated hydrocarbons, dioxane, etc. The main drawbacks with using alcohol-based solvents are that (i) a significant amount of the reaction intermediate, tetrabromocyclododecene, precipitates out of the reaction solution before the intermediate has an opportunity to be hexabrominated, and (ii) alcohols readily react with the brominating reagent to produce undesirable side-reaction products and to consume brominating reagent, generating large amounts of HBr in the process. Indeed, U.S. Pat. No. 5,292,450 reports that in isobutyl alcohol, for every mole of CDT fed to a reaction, 0.4 moles of HBr are generated. The generation of HBr in HBCD production is generally viewed as a nuisance and numerous neutralizing agents are listed in the prior art. U.S. Pat. No. 4,918,253 lists many of these neutralizing agents. Thus, the art teaches that HBr presence in the HBCD solvent is undesirable.

DE 1,147,574 and DE 1,222,049 teach the use of alcoholic (ethanol) or amide (dimethylacetamide) solvents for HBCD in the presence of "halogen carriers" such as aluminum chloride, aluminum bromide, iodine, chlorineiodide, and lithium bromide. The purpose of the halogen carriers is to boost yields. For example it is indicated that addition of aluminum chloride increases the yield of HBCD from 63% to 86%. DE 1,222,049 mentions how polar solvents such as acetonitrile, dioxane, and THF have been proven particularly ineffective as HBCD solvents. Additionally, FR 1,553,410 criticizes the use of such systems represented by DE 1,147,574 and DE 1,222,049. The French patent teaches that such a halogen carrier system generates a "resineux non cristallins" (i.e., a non-crystalline resin). EP 429,059 agrees with the French patent and reports an "insoluble resinous matter" results from such systems. Apparently, addition of the halide salts decrease the solubility of HBCD in the solvent due to the well known salting-out effect.

As for water usage in the solvent medium, it appears that water has been suggested for use as a co-solvent only with alcoholic and organic acid solvents, and then only as an aid to boost yields. Thus, U.S. Pat. No. 5,043,492 teaches the addition of 2–5% water to the alcoholic solvent to boost yields, but then further mentions that water levels greater than 5% forms a "gummy product". FR 1,553,410 allows for additions of 10% water to an acetic acid or propionic acid solvent to boost yields, but the yields are boosted by only a few percent. Thus, the art demonstrates addition of water only for slight yield increases by driving the HBCD out of the organic solvent.

It is an object of this invention to provide a process enabling the production of hexabromocyclododecane products in which the proportion of gamma isomer produced is increased relative to alpha and beta isomers. Another object is to provide process technology which makes possible the production of a highly pure hexabromocyclododecane product. A further object is to achieve at least one of the foregoing objects without forming gummy or resinous non-crystalline product. Still other objects may be seen from the following description.

SUMMARY OF THE INVENTION

Pursuant to this invention, it is now possible to achieve one or more of the foregoing objects efficiently and in a practical manner by producing hexabromocyclododecane in certain novel liquid reaction media or solvent systems which are comprised of a one or more particular types of organic solvents, water, and a suitable quantity of bromide ion.

Thus in one of its embodiments this invention provides a process which comprises brominating cyclododecatriene in a liquid medium comprised of (1) at least 50 wt % of at least one liquid inert organic solvent other than 1,4-dioxane having a solubility in water of at least 1 wt % at 25° C., and (2) water in an amount of up to about 40 wt %, in the presence of (3) about 0.5 to about 30 wt % of bromide ion (Br⁻), whereby hexabromocyclododecane is produced, each wt % being based on the total weight of the liquid portion of the liquid medium.

In another of its embodiments this invention provides a process which comprises brominating cyclododecatriene in a liquid medium comprised of (1) a predominate amount of (a) at least one halogen-free aprotic solvent other than 1,4-dioxane containing at least two oxygen atoms or at least one nitrogen atom (preferably one nitrogen atom) in the molecule, or (b) at least one liquid polyalkylene glycol in which the alkylene groups each contain two or three carbon atoms (preferably two carbon atoms) and in which the average molecular weight of the polyalkylene glycol is at least about 150 (preferably at least about 200, and more preferably in the range of about 200 to about 400) and/or at least one liquid monoalkyl ether thereof, or (c) a combination of (a) and (b), and (2) water in an amount of up to about 40 wt %, in the presence of (3) about 0.5 to about 30 wt % of bromide ion (Br⁻), each wt % being based on the total weight of the liquid portion of the liquid medium. For ease of reference, the components of (1) above, i.e., (a) at least one halogen-free aprotic solvent containing in the molecule at least two oxygen atoms (other than 1,4-dioxane) or at least one nitrogen atom (preferably one nitrogen atom), or (b) at least one liquid polyalkylene glycol in which the alkylene groups each contain two or three carbon atoms (preferably two carbon atoms) and in which the average molecular weight of the polyalkylene glycol is at least about 150 (preferably at least about 200, and more preferably in the range of about 200 to about 400) and/or at least one liquid monoalkyl ether thereof, or (c) a combination of (a) and (b), are sometimes collectively referred to hereinafter as "the Organic Solvent". It is to be noted that the polyalkylene glycols and the monoalkyl ethers thereof of (b) are not aprotic solvents whereas dialkyl ethers of polyalkylene glycols are aprotic solvents and are included in (a).

Another embodiment of this invention is a process which comprises bringing together components comprising (i) cyclododecatriene, (ii) a brominating agent, (iii) the Organic Solvent, (iv) water, and (v) a source of bromide ion (Br⁻), wherein any of (i), (ii), (iii), (iv), and (v) are fed into a reactor or reaction zone (A) concurrently, substantially concurrently, or in any sequence, and (B) in any subcombination or subcombinations of (i), (ii), (iii), (iv), or (v), with the provisos that (i) and (ii) are not brought together in the same feed or in the absence of (iii), (iv), and (v), and that at least (i) and (ii) are fed separately but concurrently or substantially concurrently into said reactor or reaction zone, whereby hexabromocyclododecane is produced.

A preferred embodiment of this invention is a process which comprises bringing together components comprising (i) cyclododecatriene, (ii) a brominating agent, (iii) the Organic Solvent, (iv) water, and (v) a source of bromide ion (Br⁻), wherein at least (i) and (ii) are brought together by feeding (i) and (ii) separately but concurrently or substantially concurrently into a reactor or reaction zone already containing (iii), (iv), (v), and optionally a small amount of (ii) to initiate bromination.

Further embodiments of this invention are each one of the above embodiments wherein diethyl ether is used as a solvent in the respective processes either in combination with the Organic Solvent or place of the Organic Solvent, and wherein the water either is used or is not used. Preferably water is used.

Still another embodiment of this invention is a liquid reaction medium comprised of about 50 to about 99 wt % of the Organic Solvent and up to about 40 wt % of water, said medium containing about 0.5 to about 30 wt % of bromide ion (Br⁻) based on the total weight of the liquids in the reaction medium. In another embodiment such reaction medium also contains cyclododecatriene as a component thereof. The foregoing reaction mixtures are adapted to provide upon the conduct of bromination therein, enhanced ratios of the gamma isomer of hexabromocyclododecane relative to the combination of the alpha and beta isomers of hexabromocyclododecane.

Yet another embodiment of this invention is the immediately preceding embodiment wherein diethyl ether is present as a solvent in the liquid reaction medium either in combination with and forming a portion of the Organic Solvent or is in place of the Organic Solvent, and wherein the water either is present or is not present. Preferably the water is present.

Other embodiments, advantages, and features of this invention will be still further apparent from the ensuing description and appended claims.

FURTHER DETAILED DESCRIPTION OF THE INVENTION

It has been discovered that by using the combination of the Organic Solvent and water together with a bromide source there is obtained, in the bromination reaction, an increase in the gamma isomer content of the reaction mass. This increased gamma isomer in the reaction slurry translates to an increase of the gamma content of the isolated solid hexabromocyclododecane (HBCD). Also achieved is good utilization of the brominating agent, e.g., bromine, due to the relative inertness of the Organic Solvent-water composition versus the typically used alcohol solvents.

While a combination of the Organic Solvent and water prevents undue consumption of the bromine due to side reactions, this system does not yield a recovered hexabromocyclododecane product having a high gamma content. Generally, the gamma content of the HBCD proportion of the reaction mass will be about 21 to 44 wt % for the Organic Solvent when used alone, and about 40 to 49 wt % for a combination of the Organic Solvent and water. It has been discovered, however, that if, in a combination of the Organic Solvent and water, the liquid portion of the reaction mass contains about 0.5 to about 30 wt % bromide ion (Br⁻), then the gamma content of the HBCD usually can be enhanced from, say, about 53 wt % up to, say, about 66 wt %. The increase in gamma isomer content of the slurry directly relates to an increase in the gamma isomer content of the isolated solid; thus producing a solid which is higher in melting point and higher in yield (due to the increased melting point and decreased solubility of the gamma isomer). Preferred amounts of bromide ion are in the range of about 4 to about 13 wt %. The wt % values for bromide are based on the total weight of the liquid portion of the reaction mass.

Although this invention is not to be limited by any theory, it is believed that the bromide ion complexes with the brominating agent, e.g., bromine, and that the resulting complex selectively assists bromination of the sterically hindered intermediates which leads to the gamma isomer. Thus, the formation of the gamma isomer is facilitated.

The process of this invention can be conducted in manners and in equipment similar to prior art processes except for the Organic Solvent-water solvent system and the use of a suitably high bromide ion content in the liquid portion of the reaction mass.

The brominating agent is preferably liquid bromine which is added as such to the reactor. It is within the scope of this invention, however, to produce the bromine in situ. For example, HBr can be fed to the reactor along with an oxidant such as $H_2O_2$ which will convert HBr to $Br_2$. Since HBr is a good source for the bromide ion feature of this invention, this mode of operation can be attractive as the HBr can be provided in an amount which fulfills both the $Br_2$ and the bromide ion needs. Moreover, use of HBr as the bromine source avoids the storage and handling of elemental bromine. The $Br_2$ and HBr used should both be of good quality and essentially free of impurities. Commercially available grades of either of these two compounds are generally suitable.

It is possible to form the HBr in situ by use of a water-soluble bromide salt (e.g., LiBr, NaBr, KBr, etc.) and a suitable acid such as sulfuric acid or phosphoric acid. Thus the bromination can be performed using preexisting elemental bromine or using bromine formed in situ.

The cyclododecatriene should also have a good quality and can be provided by most commercial grades of this compound. The usual molecular configuration of the cyclododecatriene corresponds to 1,5,9-cis,trans,trans-cyclododecatriene. However the actual isomeric configuration of the cyclododecatriene is not deemed critical to the practice of this invention.

Quantitatively, the relationship between the amounts of cyclododecane and brominating agent is essentially stoichiometric to yield hexabromocyclododecane. Thus, if the brominating agent is $Br_2$, then three moles of $Br_2$ per mole of cyclododecatriene will be used. If, however, the brominating agent contains but a single Br constituent, then six moles per mole of cyclododecatriene will be used. The same 6:1 molar ratio applies if HBr is used to produce $Br_2$ in situ as discussed above. It is preferred to provide a small excess of brominating agent. Up to about 10% excess of stoichiometric is suitable, with about 2 to about 8% being preferred and about 2 to about 7% being most preferred. Amounts of brominating agent in excess of the just-mentioned 10% may be used, but they are not preferred as they appear to confer no significant benefit.

The Organic Solvent used in the practice of this invention most preferably contain no or very little alcohol or other species reactive species, say less than 5 wt %. In this connection, by "alcohol" whether used in the singular or plural, is meant an aliphatic solvent containing only hydroxyl functionality and having less than 10 carbon atoms, such as, for example, ethyl alcohol, n-propyl alcohol, isopropyl alcohol, n-butyl alcohol, isobutyl alcohol, sec-butyl alcohol, and alkanediols such as 1,2-ethanediol (ethylene glycol), 1,2-propanediol, 1,3-propanediol, 1,4-butanediol, and the like.

The Organic Solvent preferably has a solubility in water above 1 wt % at 25° C. and thus for the purposes of this invention, the preferred solvent(s) used with water can be referred to alternatively as at least one organic solvent having a solubility in water of greater than 1 wt % at 25° C., and which more preferably contains no or very little alcohol or other reactive species, say, less than 5 wt %. Non-limiting examples of suitable solvents suitable for use as the Organic Solvent include ethers (e.g., 1,2-dimethoxyethane, diethyl ether, 1,2-diethoxyethane); esters (e.g., ethyl acetate, ethyl propionate, n-propyl acetate, isopropyl acetate, ethylene glycol diacetate, ethyl formate, butyrolactone); nitriles (e.g., acetonitrile); carbonates (e.g., ethyl carbonate); polyethylene glycols with average molecular weights of at least 150, preferably at least about 200, and more preferably in the range of about 200 to about 400; polyethylene glycol mono- or dialkyl ethers formed from polyethylene glycols that have the foregoing average molecular weights and where the alkyl group or groups each contain 1 to 4 and preferably 1 or 2 carbon atoms; polypropylene glycols with average molecular weights of at least 150, preferably at least about 200, and more preferably in the range of about 200 to about 400; polypropylene glycol mono- or dialkyl ethers formed from polypropylene glycols that have the foregoing average molecular weights and where the alkyl group or groups each contain 1 to 4 and preferably 1 or 2 carbon atoms; and mixtures of any two or more such solvents. The foregoing polyethylene glycols and polypropylene glycols (whether used as such or in the form of mono- or dialkyl ethers thereof, or both), can have still higher average molecular weights, e.g., as high as 600 or more, provided that these substances are used in combination with another solvent such as diethyl ether to reduce the viscosity of the solvent and the resultant reaction mixture in which such substances are used. Similarly, it can be preferable to use a low viscosity organic solvent with polyethylene glycols and polypropylene glycols (whether used as such or in the form of mono- or dialkyl ethers thereof, or both) having average molecular weights of about 400 and below so as to reduce the viscosities of the solvent and the resultant reaction mixture.

A characteristic of the ester solvents tested to date is their propensity to produce HBCD product containing relatively small, but significant, amounts (e.g., 3 to 5 wt %) of tetrabromo species (presumably one or more tetrabromocyclododecene species) within the crystalline structure of the product. Apparently use of these ester solvents, at least in the absence of other solvents used in the practice of this invention, results in co-precipitation of the tetrabromo species along with the HBCD enriched in gamma isomer. Such product would no doubt be entirely suitable for use as a flame retardant in polymers.

When using acetonitrile it was found, under the processing conditions used, to be essentially inert to a mixture of bromine, HBr, and water. However it did produce a residue after evaporation. The reason for this is not presently known. Perhaps the supply used had been contaminated with a residue-producing substance. Nevertheless, acetonitrile can be used successfully in the practice of this invention, and if such residues are in fact formed under the processing conditions used, it would appear desirable to forego reuse or recycle of this solvent in the process.

Dimethoxyethane, if used, is preferably used at low temperatures, say, about 5° C. or below and/or as a minor component of a solvent mixture with another solvent, as it tends even at ambient room temperature conditions to release some methyl bromide.

Solvents other than those identified above may be found useful in the practice of this invention. Thus in any case where the suitability of any solvent proposed for use with or without the solvents identified above, one should perform one or two preliminary experiments using a procedure such as described in the Examples hereinafter to thereby assess the suitability of the proposed solvent.

As indicated above, diethyl ether can be used either with or without water as long as the there is present about 0.5 to about 30 wt % of bromide based on the total weight of the liquid portion of the liquid medium. Preferably water is present in the liquid medium because in the absence of water it is more difficult and time-consuming to include bromide in diethyl ether. Typically to include bromide in diethyl ether involves sparging HBr into the diethyl ether. Whether hydrogen bromide is ionized in pure diethyl ether is not presently known. It is known however that diethyl ether can be used in the absence of deliberately added amounts of water after having been sparged with HBr (note Example XII hereinafter). The term "deliberately added" is used herein because as in practice, especially on a commercial scale, it is at least extremely difficult, to prevent at least one molecule of water of finding its way into a solvent. Thus even though solvents are deemed "anhydrous" there can be trace amounts of water present therein. Accordingly, the diethyl ether when used without deliberately added water in the practice of this embodiment of the invention, may contain trace impurity amounts of water.

Besides containing no or very little alcohol or other reactive species, say less than 5 wt %, the mixture of the Organic Solvent and water preferably contains at least about 50 wt % of the Organic Solvent and no more than about 40 wt % of water. More preferred mixtures of the Organic Solvent and water are those which contain up to about 40 wt % of water and about 99 to about 60 wt % of the Organic Solvent. Still more preferably, the mixtures of the Organic Solvent and water will contain up to about 20 wt % water and about 95 to about 80 wt % polar solvent. For the above described solvents, the weight percentages are based on the total weight of the water and of the component(s) of the Organic Solvent. The component or each of the components of the Organic Solvent used in forming such mixtures with water is preferably of a commercial quality and more preferably it should be of a purity of at least 95 wt %. Most preferably the component or each of the components of the Organic Solvent used will have a purity of 98+ wt %.

It is not impermissible for the solvents of this invention to contain some alcohol or other reactive species provided that the amount of such solvents does not deprive the process of benefits from using a mixture of water and the Organic Solvent. However, it is more preferred that the solvents of this invention be essentially free of alcohol or reactive species. By reactive species is meant species that are more reactive in the process than is the Organic Solvent that has been chosen for use.

It is not impermissible for the solvents of this invention to contain some water-insoluble solvent species, i.e., inert organic solvents that have a solubility in water at 25° C. of 1 wt % or less, provided that the amount of such solvents does not deprive the process of benefits from using a mixture of water and the Organic Solvent. However, it is more preferred that the solvents of this invention be essentially free of such water-insoluble solvent species. Due to solubility issues with water, HBr, and bromide salts, such water-insoluble solvents themselves are not used for the purpose of providing enhanced gamma isomer; however, suitably small amounts of non-polar solvent (e.g., 5 wt % or less) may constitute part of a solvent mixture, as long as it causes no harm to the process. Non-limiting examples of such water-insoluble solvents are haloalkanes (e.g., methylene chloride, ethylene dichloride, bromochloromethane), aromatic hydrocarbons (e.g., benzene, toluene, chlorobenzene), and saturated aliphatic or cycloaliphatic hydrocarbons (e.g., pentane, hexane, heptane, cyclopentane, cyclohexane, methylcyclopentane).

The bromide ion can be provided to the reaction mass by way of a bromide ion source which is soluble in the reaction mass under process conditions and which yields bromide ion under such conditions. Exemplary bromide ion sources are alkali metal bromide, alkaline earth metal bromide, organic bromide and mixtures of any two or more of the foregoing. Preferred are HBr, LiBr, NaBr or mixtures thereof. The HBr can be added directly to the reaction mass or can accompany the solvent system. For example, the solvent system can be produced from the Organic Solvent and aqueous HBr or the solvent system can be a recycled mother liquor from a previously run batch which contains HBr from prior direct additions and/or from in situ formation of HBr from the bromination of reaction mass species. If the bromide ion source is LiBr or NaBr, then it is simply added to the reaction mass. The particular identity of the bromide ion source is not critical to the process of this invention so long as it does not deleteriously affect the process and can effectively yield the desired level of bromide ion. The bromide ion can also be generated in situ via chemical or electrochemical action.

The processes of this invention are preferably practiced by first charging a reactor with the Organic Solvent-water mixture and bromide ion. To this initial charge is preferably added a pre-charge of brominating agent, which pre-charge will count against the total brominating agent used in the process. Cyclododecatriene and further brominating agent are then fed, preferably concurrently or substantially concurrently as separate feeds to the reactor. Throughout the cyclododecatriene and brominating agent feeds, the reaction mass is kept at a temperature between about 0° C. and about 80° C., and preferably below or equal to about 60° C. Most preferred temperatures are in the range of about 20 to about 60° C. Most highly preferred are temperatures in the range of about 20 to about 55° C. Temperatures much above about 80° C. will tend to retard the desired production of the gamma stereoisomer even in the presence of the bromide ion. The reaction pressure is not critical, with near atmospheric or atmospheric pressures being preferred.

When using the preferred practice of pre-charging a portion of the bromine to the reactor before the cyclododecatriene and main bromine feeds are initiated, the amount of the pre-charge is preferably in the range of about 1 to about 10% of the total bromine used in the process. A more preferred pre-charge will be in the range of about 2 to about 7% of the total bromine.

It is preferred that the cyclododecatriene and the brominating agent feeds occur concurrently (i.e., at the same time) or substantially concurrently, (i.e., at least partially at the same time). It is most preferred that the periods of the two feeds be essentially, say 80+% of the time, simultaneous. Fully simultaneous feeds are highly preferred. The cyclododecatriene and brominating agent are preferably fed separately, simultaneously and from adjacent or spaced apart points of feed. Optionally, the brominating agent and/or cyclododecatriene may be fed into a circulating loop of reaction mixture instead of being fed directly into the reactor. For economical reasons it is preferred to simply inject the reagents into the reactor. While it is beneficial to have the cyclododecatriene and brominating feeds occur together for at least some portion of the feed period, it is possible to pre-charge all of the bromine or cyclododecatriene to the reactor and to then add the other reagent over time. This latter feeding technique, while usable, is not preferred as it can result in reaction hot spots which can cause product quality and operational problems. In all cases, it is preferred that the brominating agent and cyclododecatriene be fed subsurface, say a few inches under the reaction mass surface, of the reaction mass in the reactor. The use of jet feeding for both reactants is preferred as it contributes to their facile and quick mixing. Any jet velocity that assists in providing the amount of mixing desired, e.g., on the order of about 0.3 to about 10 ft/sec, can be used. In all cases the reactor should provide stirring, the overall object being the thorough mixing of the reactor contents.

After the cyclododecatriene and bromine feeds are finished, the reaction mass typically will be a slurry containing hexabromocyclododecane (precipitate and solute), polar solvent/water composition, bromide ion, unreacted bromine and partially brominated cyclododecatrienes (precipitate and solute), the latter being predominately tetrabromocyclododecenes, say, about 5 to about 15 wt % (the wt % being based on the total amount of brominated cyclododecatriene present in the reaction mass at that time). Most of the partially brominated cyclododecatrienes are solutes in the liquid phase of the reaction mass. The solid phase of the reaction mass is an easily recovered hexabromocyclododecane product precipitate.

It may be desirable, depending upon the economics of any particular process of this invention, to convert at least a part of the underbrominated cyclododecatriene to hexabromocyclododecane. Simple heating of the reaction mass will convert a significant amount of the tetrabromocyclododecene solutes in the reaction mass to hexabromocyclododecane. The heating step is without significant downside in the processes of this invention as the solvent/water composition, when free of alcohol and other reactive species, does not react with reaction mass constituents which is unlike the situation which occurs when the solvent is or contains a large amount of a reactive species, such as an alcohol. Thus, an advantage for the solvents of this invention is that a highly pure product containing no or little solvent derived by-products can be obtained directly without the need for further purification steps, e.g., recrystallization, which is indicated for systems using a reactive solvent such as alcohol.

The optional thermal finishing step is preferably performed without a work-up of the reaction mass. It is convenient to simply leave the reaction mass, as is, in the reaction vessel and to then apply heat for the desired period of time. Suitable reaction mass temperatures for the thermal finishing step are in the range of about 70 to about 90° C., and preferably in the range of about 70 to about 80° C. The reaction mass is maintained at the elevated temperature for a period of time so that the desired amount of tetrabromocyclododecenes are converted to hexabromocyclododecane. Generally, the heat-treatment temperature is maintained for a period of about 1 to about 180 minutes, and preferably about 1 to about 60 minutes. The shorter times are useful when the tetrabromocyclododecene content of the reaction mass is low, the longer times being useful when the tetrabromocyclododecene content is higher. The use of a heat treatment step is indicated if the process without heat treatment does not provide a desired low level of tetrabromocyclododecene in the recovered hexabromocyclododecane product.

Depending upon the cost allocable to heating of the reaction mass for the finishing step versus the cost of process time, it could be desirable to simply let the reaction mass come to about ambient temperature and sit for an extended period of time to await conversion of residual tetrabromocyclododecenes to hexabromocyclododecane. This technique will not be economically favored in most cases.

After the thermal finishing step or after the brominating agent and cyclododecatriene feeds are completed, if no finishing step is used, the reaction mass is preferably allowed to cool to about ambient room temperature. The liquid phase and the solid phase of the reaction mass are then conventionally separated, e.g., by centrifugation, decantation or filtration. A final hexabromocyclododecane product can be obtained by simply water washing the separated solid phase, i.e. the precipitated hexabromocyclododecane product. It is preferred, however, to wash the precipitated hexabromocyclododecane product with a solvent in addition to the water.

Depending on the solubility of the HBCD product in the reaction slurry formed by use of a given mixture of the Organic Solvent and water, it may be desirable to improve yields through post-addition of a non-polar solvent and/or water in order to precipitate additional HBCD product. This addition of non-polar solvent and/or water is not required to obtain a commercial product and the determination to post-add solvent and/or water to the reaction mass is based on several criteria including yield improvement, ease of non-polar solvent recovery, and cost of the non-polar solvent.

Various methods can be used for isolating the hexabromocyclododecane product. In most cases, the various techniques that are available for use merely change the nature and economics of the isolated product, they do not however improve the quantity of gamma isomer in the product slurry in the first place.

If needed to remove acidic components from the precipitate, e.g., HBr, the precipitate can be washed to at least near neutrality with a dilute base, say aqueous ammonium hydroxide. After all washing has been accomplished, the washed precipitate is oven dried at a temperature in the range of about 90 to about 115° C.

Hexabromocyclododecane product yields can be increased by recycling the mother liquor, the wash liquor and their respective unfiltered solids to subsequent reactions.

The processes of this invention can be run in the batch, semi-continuous or continuous modes.

All analytical determinations of product composition (as weight percentages) referred to in this document utilized the following procedure: The ratio of the hexabromocyclododecane isomers were determined by high pressure liquid chromatography. The sample is prepared in tetrahydrofuran/acetonitrile solvent at a concentration of 10 mg/ML. The dilute solution is injected onto a Zorbax ODS 4.6 mm×250 mm column maintained at 20° C. The eluent is acetonitrile/water, 80/20, v/v at a flow rate of 1 mL/min. Detection was made by a Hitachi L-4000 UV detector at 220 nm. Recording and integration were accomplished by a Hewlett Packard 3396A integrator. The response factor of all components were assumed to be equal. The retention times of the three hexabromocyclododecane isomers are: alpha (12.1 min.), beta (13.6 min.), and gamma (19.3 min.).

The hexabromocyclododecane products of this invention are suitable for use as flame retardants in thermoplastic formulations. They are useful, for example, in high impact polystyrene, expanded polystyrene, extruded polystyrene, polypropylene and epoxy thermosets. The products are also useful in textiles, paints and hot melts. In the foregoing applications, conventional loadings are useful and conventional additives, such as synergists, antioxidants, pigments, fillers, acid scavengers and UV stabilizers may also be used in conventional amounts. Preferred loadings for the hexabromocyclododecane products of this invention are in the range of about 0.8 to about 3 wt %, the wt % being based upon the total weight of the thermoplastic formulation.

The following Examples, wherein all parts and percentages are by weight unless specified otherwise, are illustrative of the processes this invention. The Examples are not intended to limit, and should not be construed as limiting, the scope of the invention.

EXAMPLE I

A 500 mL multi-neck round bottom flask was charged with 90 g of neat 1,2-diethoxyethane and 25 g of aqueous 60% HBr (0.19 mol HBr). Cyclododecatriene (CDT) (30 g, 0.19 mol, 50% loading) and bromine (93.3 g, 0.58 mol) were primed for co-feed. Part of the bromine (3 g) was pre-charged to the reactor before beginning the CDT feed. Feed rates for the CDT and bromine were adjusted so that both feeds ended nearly simultaneously. The reaction temperature did not exceed 28° C. during the feeding period. For convenience of the operator, the reaction mass was then stirred at ambient conditions overnight. At this point it was determined that a thermal finishing step would be suitable in order to convert some of the tetrabromocyclododecene intermediates into additional product. Thus, the reaction mass was maintained at 75–80° C. for approximately 180 minutes. After this period the reaction mass was allowed to cool to ambient temperature. 750 mg of Monawet MO-70 (sodium dioctyl sulfosuccinate, Mona Industries, Inc.), 50 mL hexane, 5 mL saturated sodium sulfite solution, and 150 mL water were all added to the reaction mass. The reaction mass was the vacuum filtered and washed with excess water and 25 mL hexane. The white solid was then oven dried at 90° C. to yield a fine white powder (109 g, 92% yield). The yield was based on the moles of hexabromocyclododecane product recovered per mole of cyclododecatriene used in the reaction. The solid melts 186–196° C. and has the following isomer composition (wt %): 12.1% alpha, 9.1% beta, 77.2% gamma.

was charged slightly ahead of the CDT for a total pre-charge of 1.5 g. At feed completion, the ice bath was removed and the slurry stirred for 15 min. before a 70° C. water bath was used to warm the reaction slurry for 15 min. HPLC analysis of the slurry was taken at this point. This description is for a 40% loading experiment; different loadings were accomplished by adjusting the solvent charge.

TABLE I

|  | II | III | IV | V | VI | VII | VIII | IX |
|---|---|---|---|---|---|---|---|---|
| solvent* | glyme | glyme | glyme | PEG 400 | PEG 400 | polyglyme | polyglyme | polyglyme |
| % solvent** | 100.00 | 80.00 | 90.00 | 100.00 | 90.00 | 100.00 | 90.00 | 90.00 |
| wt % HBr | 0.00 | 0.00 | 13.00 | 0.00 | 13.00 | 0.00 | 13.00 | 13.00 |
| wt % loading | 40.00 | 40.00 | 40.00 | 40.00 | 40.00 | 40.00 | 40.00 | 30.00 |
| % alpha isomer | 20.50 | 12.40 | 15.10 | 11.80 | 13.80 | 7.20 | 14.10 | 12.30 |
| % beta isomer | 29.40 | 20.30 | 10.00 | 13.10 | 10.50 | 17.20 | 9.60 | 7.60 |
| % gamma isomer | 27.70 | 40.30 | 63.90 | 28.10 | 58.80 | 20.60 | 62.20 | 62.70 |
|  | X | XI | XII | XIII | XIV | XV | XVI | XVII |
| solvent* | ether | ether | ether | ether | EtOAc | EtOAc | EtOAc | EtOAc |
| % solvent** | 80.00 | 90.00 | 100.00 | 90UU | 100.00 | 90.00 | 90.00 | 90.00 |
| wt % HBr | 0.00 | 13.00 | 7.00 | 13.00 | 0.00 | 0.00 | 13.00 | 13.00 |
| wt % loading | 40.00 | 40.00 | 40.00 | 60.00 | 40.00 | 40.00 | 40.00 | 50.00 |
| % alpha isomer | 15.30 | 17.00 | 15.50 | 15.30 | 9.40 | 13.80 | 15.10 | 14.90 |
| % beta isomer | 24.00 | 14.80 | 14.10 | 15.80 | 27.50 | 24.00 | 17.70 | 19.10 |
| % gamma isomer | 47.30 | 59.60 | 59.80 | 58.60 | 35.40 | 46.90 | 59.00 | 57.30 |
|  | XVIII | XIX | XX | XXI | XXII | XXIII | XXIV | XXV |
| solvent* | EGDA | EGDA | CH3CN | CH3CN | CH3CN | CH3CN | Et formate | Et formate |
| % solvent** | 100.00 | 90.00 | 100.00 | 90.00 | 90.00 | 90.00 | 100.00 | 90.00 |
| wt % HBr | 0.00 | 13.00 | 0.00 | 0.00 | 5.00 | 13.00 | 0.00 | 13.00 |
| wt % loading | 40.00 | 40.00 | 40.00 | 40.00 | 40.00 | 40.00 | 40.00 | 40.00 |
| % alpha isomer | 10.30 | 15.70 | 12.40 | 12.80 | 15.90 | 15.70 | 13.10 | 14.50 |
| % beta isomer | 28.40 | 18.90 | 30.60 | 14.30 | 16.70 | 17.00 | 33.50 | 19.60 |
| % gamma isomer | 33.30 | 56.10 | 25.70 | 47.60 | 58.80 | 57.60 | 44.00 | 59.60 |

*Glyme (1,2-dimethoxyethane), PEG 400 (polyethylene glycol, 400 ave. molecular wt.), polyglyme (polyethylene glycol dimethyl ether, 250 ave. molecular wt.), ether (diethyl ether), EtOAc (ethyl acetate), EDAC (ethylene glycol diacetate), CH3CN (acetonitrile), Et formate (ethyl formate).
**Percent solvent refers to the amount of solvent in a solvent/water mixture. 100% solvent describes neat solvent.

EXAMPLES II–XXV

This general procedure was followed to obtain the isomer data presented in Table I. The reactor used was a four-neck, mini-lab flask head mated to a 100 mL open-neck flask. A typical experiment follows: The flask was charged with 39.1 g glyme (1,2-dimethoxyethane) and 810.9 g 60% aqueous HBr (13% HBr based on solvent charge). An ice bath was used to chill the contents to 10° C. at which time the co-feeds were started. Bromine (26.2 g, 5% xs) and CDT (8.4 g, 40% loading) were fed subsurface through 1/32" teflon tubing at flow rates of 1.0 and 1.2 mL/min respectively. The bromine HBCD product produced using the processes of this invention when isolated as in Example I are white crystalline solids which when dried are free flowing unlike gummy or resinous non-crystalline product formed in certain prior art processes referred at the outset.

Compounds referred to by chemical name anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

Each and every patent, publication, or commonly-owned patent application referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process which comprises brominating cyclododecatriene in a liquid medium comprised of (1) at least 50 wt % of at least one liquid inert organic solvent other than 1,4-dioxane having a solubility in water of at least 1 wt % at 25° C., and (2) water in an amount of up to about 40 wt %, in the presence of (3) about 0.5 to about 30 wt % of bromide ion (Br$^-$), whereby hexabromocyclododecane is produced, each wt % being based on the total weight of the liquid portion of the liquid medium, wherein said at least one liquid inert organic solvent consists essentially of (a) at least one halogen-free aprotic solvent containing at least two oxygen atoms or at least one nitrogen atom in the molecule other than 1,4-dioxane, or (b) at least one liquid polyalkylene glycol in which the alkylene groups each contain two or three carbon atoms and in which the average molecular weight of the polyalkylene glycol is at least about 150 and/or at least one liquid monoalkyl ether thereof, or (c) a combination of (a) and (b).

2. A process according to claim 1 wherein the bromination is conducted at one or more temperatures in the range of about 0° C. to about 60° C.

3. A process according to claim 1 wherein the bromination is conducted at one or more temperatures in the range of about 20° C. to about 55° C.

4. A process according to claim 1 wherein the bromination is performed using preexisting elemental bromine.

5. A process according to claim 1 wherein the bromination is performed using bromine formed in situ.

6. A process according to claim 1 wherein in (a) said at least one halogen-free aprotic solvent containing at least one nitrogen atom is at least one halogen-free aprotic solvent that contains only one nitrogen atom in the molecule, wherein in (b) said at least one liquid polyalkylene glycol in which the alkylene groups each contain two or three carbon atoms is at least one liquid polyalkylene glycol in which the alkylene groups each contain only two carbon atoms, and wherein in (b) said average molecular weight of said polyalkylene glycol is at least about 200.

7. A process according to claim 6 wherein in (b) said average molecular weight of said polyalkylene glycol is in the range of about 200 to about 400.

8. A process according to claim 1 where in the liquid inert organic solvent that is used in said process consists essentially of (I) at least one liquid polyethylene glycol, (II) at least one liquid polyethylene glycol monoether, (III) at least one liquid polyethylene glycol dimethyl ether, or any mixture of two or more of (I), (II), and (III), wherein each of (I), (II) and (III) has an average molecular weight in the range of about 200 to about 400.

9. A process according to claim 1 where in the liquid inert organic solvent that is used in said process consists essentially of at least one liquid polyethylene glycol dimethyl ether having an average molecular weight in the range of about 200 to about 400.

10. A process according to claim 1 where in the liquid inert organic solvent that is used in said process consists essentially of a combination of at least (A) at least one liquid polyalkylene glycol in which the alkylene groups each contain two or three carbon atoms having an average molecular weight above about 400 and/or a mono- or dialkyl ether thereof, and (B) at least one other liquid inert organic solvent that reduces the viscosity of said liquid medium.

11. A process according to claim 1 where in the liquid inert organic solvent that is used in said process consists essentially of at least one liquid inert organic ester.

12. A process according to claim 1 where in the liquid inert organic solvent that is used in said process consists essentially of at least one liquid inert nitrile.

13. A process according to claim 11 wherein said liquid inert organic ester consists essentially of ethyl acetate, ethylene glycol diacetate, ethylformate, or a mixture of any two or all three of them.

14. A process according to claim 11 wherein said liquid inert nitrile consists essentially of acetonitrile.

15. A process according to claim 1 wherein the process is conducted so that a batch of reaction mass containing hexabromocyclododecane has been formed upon completion of the bromination, and wherein said batch of reaction mass is subjected to a thermal finishing step at one or more temperatures in the range of about 70 to about 90° C.

16. A process according to claim 15 wherein said one or more temperatures in the range of about 70 to about 90° C. are maintained for a period in the range of about 1 to about 60 minutes.

17. A process according to claim 16 wherein the bromination is conducted at one or more temperatures in the range of about 0° C. to about 60° C.

18. A process which comprises bringing together in a reactor or reaction zone components comprising (i) cyclododecatriene, (ii) a brominating agent, (iii) a liquid inert organic solvent that is (a) at least one halogen-free aprotic solvent containing in the molecule at least two oxygen atoms or at least one nitrogen atom other than 1,4-dioxane, or (b) at least one liquid polyalkylene glycol in which the alkylene groups each contain two or three carbon atoms and in which the average molecular weight of the polyalkylene glycol is at least about 150, and/or at least one liquid monoalkyl ether thereof, or (c) a combination of (a) and (b), (iv) water, and (v) a source of bromide ion (Br$^-$), wherein any of (i), (ii), (iii), (iv), and (v) are fed into the reactor or reaction zone (A) concurrently, substantially concurrently, or in any sequence, and (B) in any subcombination or subcombinations of (i), (ii), (iii), (iv), or (v), with the provisos that (i) and (ii) are not brought together in the same feed or in the absence of (iii), (iv), and (v), and that at least (i) and (ii) are fed separately but concurrently or substantially concurrently into said reactor or reaction zone, whereby hexabromocyclododecane is produced.

19. A process according to claim 18 wherein in (b) said average molecular weight of said polyalkylene glycol is in the range of about 200 to about 400.

20. A process according to claim 18 wherein the liquid inert organic solvent that is used in said process consists essentially of (I) at least one liquid polyethylene glycol, (II) at least one liquid polyethylene glycol monoether, (III) at least one liquid polyethylene glycol dimethyl ether, or any mixture of two or more of (I), (II), and (III), wherein each of (I), (II) and (III) has an average molecular weight in the range of about 200 to about 400.

21. A process according to claim 18 wherein the liquid inert organic solvent that is used in said process consists essentially of at least one liquid polyethylene glycol dimethyl ether having an average molecular weight in the range of about 200 to about 400.

22. A process according to claim 18 wherein the liquid inert organic solvent that is used in said process consists essentially of at east one liquid inert organic ester.

23. A process according to claim 18 wherein the liquid inert organic solvent that is used in said process consists essentially of at least one liquid inert nitrile.

24. A process according to claim 22 wherein said liquid inert organic ester consist essentially of ethyl acetate, ethylene glycol diacetate, ethylformate, or a mixture of any two or all three of them.

25. A process according to claim 23 wherein said liquid inert nitrile consists essentially of acetonitrile.

26. A process according to claim 18 wherein the process is conducted so that a batch of reaction mass containing hexabromocyclododecane has been formed upon completion of the bromination, and wherein said batch of reaction mass is subjected to a thermal finishing step at one or more temperatures in the range of about 70 to about 90° C. for a period in the range of about 1 to about 60 minutes.

27. A process according to claim 26 wherein the bromination is conducted at one or more temperatures in the range of about 0° C. to about 60° C.

28. A process which comprises bringing together in a reactor or reaction zone components comprising (i) cyclododecatriene, (ii) a brominating agent, (iii) a liquid inert organic solvent that is (a) at least one halogen-free aprotic solvent containing in the molecule at least two oxygen atoms or at least one nitrogen atom other than 1,4-dioxane, or (b) at least one liquid polyalkylene glycol in which the alkylene groups each contain two or three carbon atoms and in which the average molecular weight of the polyalkylene glycol is at least about 150, and/or at least one liquid monoalkyl ether thereof, or (c) a combination of (a) and (b), (iv) water, and (v) a source of bromide ion ($Br^-$), wherein at least (i) and (ii) are brought together by feeding (i) and (ii) separately but concurrently or substantially concurrently into the reactor or reaction zone already containing (iii), (iv), (v), and optionally a small amount of (ii).

29. A process according to claim 28 wherein the liquid inert organic solvent that is used in said process consists essentially of (I) at least one liquid polyethylene glycol, (II) at least one liquid polyethylene glycol monoether, (III) at least one liquid polyethylene glycol dimethyl ether, or any mixture of two or more of (I), (II), and (III), wherein each of (I), (II) and (III) has an average molecular weight in the range of about 200 to about 400.

30. A process according to claim 28 wherein the liquid inert organic solvent that is used in said process consists essentially of at least one liquid polyethylene glycol dimethyl ether having an average molecular weight in the range of about 200 to about 400.

31. A process according to claim 28 wherein the liquid inert organic solvent that is used in said process consists essentially of at least one liquid inert organic ester.

32. A process according to claim 28 wherein the liquid inert organic solvent that is used in said process consists essentially of at least one liquid inert nitrile.

33. A process according to claim 31 wherein said liquid inert organic ester consists essentially of ethyl acetate, ethylene glycol diacetate, ethylformate, or a mixture of any two or all three of them.

34. A process according to claim 32 wherein said liquid inert nitrile consists essentially of acetonitrile.

35. A process which comprises brominating cyclododecatriene in a liquid medium comprised of at least 50 wt % of diethyl ether in the presence of about 0.5 to about 30 wt % of bromide, whereby hexabromocyclododecane is produced, each wt % being based on the total weight of the liquid portion of the liquid medium.

36. A process according to claim 35 wherein no water is deliberately introduced into said medium.

37. A process according to claim 35 wherein no water is deliberately introduced into said medium such that said medium contains up to about 40 wt % of water during bromination.

38. A process according to claim 35 wherein no organic solvent other than the diethyl ether is used in the bromination.

39. A process according to claim 38 wherein no water is deliberately introduced into said medium.

40. A process according to claim 38 wherein water is deliberately introduced into said medium such that said medium contains up to about 40 wt % of water during bromination.

41. A process according to claim 35 wherein the bromination is conducted at one or more temperatures in the range of about 0° C. to about 60° C.

42. A process according to claim 35 wherein the bromination is conducted at one or more temperatures in the range of about 20° C. to about 55° C.

43. A process according to claim 35 wherein the bromination is performed using preexisting elemental bromine.

44. A process according to claim 35 wherein the bromination is performed using bromine formed in situ.

* * * * *